United States Patent [19]

Haas

[11] Patent Number: 4,861,797
[45] Date of Patent: Aug. 29, 1989

[54] LIQUID IBUPROFEN COMPOSITIONS AND METHODS OF MAKING THEM

[75] Inventor: Ronald T. Haas, West Windsor Township, Mercer County, N.J.

[73] Assignee: Oratech Pharmaceutical Development Corporation, Princeton, N.J.

[21] Appl. No.: 110,184

[22] Filed: Oct. 15, 1987

[51] Int. Cl.$^4$ .............................................. A61K 31/19
[52] U.S. Cl. .................................................... 514/557
[58] Field of Search ............... 424/485, 486, 484, 456, 424/488; 514/557

[56] References Cited

U.S. PATENT DOCUMENTS

| | | |
|---|---|---|
| 3,041,239 | 6/1962 | Nashed . |
| 3,228,831 | 1/1966 | Nicholson et al. . |
| 3,385,886 | 5/1968 | Nicholson et al. . |
| 3,733,410 | 5/1973 | Asche . |
| 3,903,297 | 9/1975 | Robert . |
| 3,911,137 | 10/1975 | Miki et al. . |
| 3,927,205 | 12/1975 | Ohno et al. . |
| 4,031,243 | 6/1977 | Aparicio et al. . |
| 4,145,440 | 3/1979 | Fitch et al. . |
| 4,282,252 | 8/1981 | Lefer . |
| 4,344,929 | 8/1972 | Bonsen et al. . |
| 4,346,108 | 8/1982 | Singer . |
| 4,361,580 | 11/1982 | Peck et al. . |
| 4,389,393 | 6/1983 | Schor et al. . |
| 4,404,210 | 9/1983 | Schmidt . |
| 4,439,450 | 3/1984 | Coleman . |
| 4,447,443 | 5/1984 | Goldenberg . |
| 4,447,451 | 5/1984 | Mueller . |
| 4,536,595 | 8/1985 | Gardano et al. . |
| 4,545,992 | 10/1985 | Kamashita . |
| 4,552,899 | 11/1985 | Sunshine et al. . |
| 4,555,524 | 11/1985 | Gruber et al. . |
| 4,558,051 | 12/1985 | Sunshine et al. . |
| 4,569,937 | 2/1986 | Baker et al. . |
| 4,571,400 | 2/1986 | Arnold . |
| 4,587,252 | 5/1986 | Arnold . |
| 4,599,359 | 7/1986 | Cooper . |
| 4,609,675 | 9/1986 | Franz . |
| 4,619,934 | 10/1986 | Sunshine et al. . |
| 4,681,897 | 7/1987 | Brand . |
| 4,684,666 | 8/1987 | Haas ..................................... 514/557 |
| 4,687,662 | 8/1987 | Schobel . |
| 4,689,218 | 8/1987 | Gazzaniga et al. . |
| 4,690,823 | 9/1987 | Lohner et al. . |
| 4,695,591 | 9/1987 | Hanna et al. ................... 424/488 X |
| 4,713,249 | 12/1987 | Schroder . |
| 4,717,713 | 1/1988 | Zatz et al. . |
| 4,726,966 | 2/1988 | Kawashima et al. . |
| 4,788,220 | 11/1988 | Mody et al. ........................ 514/557 |

FOREIGN PATENT DOCUMENTS

| | | |
|---|---|---|
| 1197254 | 11/1986 | Canada . |
| 0068838 | 1/1983 | European Pat. Off. . |
| 0137668 | 4/1985 | European Pat. Off. . |
| 2000322 | 7/1970 | Fed. Rep. of Germany . |
| 2400363 | 3/1979 | France . |
| 867803 | 5/1961 | United Kingdom . |
| 2079600 | 1/1982 | United Kingdom . |

OTHER PUBLICATIONS

Moore et al., "Postextraction Pain Relief in Children: A Clinical Trial of Liquid Analgesics", *International Journal of Clinical Pharmacology, Therapy and Toxicology*, vol. 23, No. 11-1985, pp. 573-577.

Morrison et al., *Organic Chemistry*, Third Edition, 1973, pp. 579-584.

Norman et al., "A Double-Blind Comparison of a New Ibuprofen-Codeine Phosphate Combination, Codeine Phosphate, and Placebo in the Relief of Postepisiotomy Pain", *Clinical Therapeutics*, vol. 7, No. 5, 1985, pp. 549-554.

Adams et al., "The Pharmacological Properties of Ibuprofen, An Anti-Inflammatory, Analgesic and Anti-Pyretic Agent", *Arch. Int. Pharmacodyn.*, 1969, vol. 178, No. 1, pp. 115-129.

Glenn et al., "In Vitro Effects of Non-Steroidal Anti--Inflammatory Drugs (NAIFD)", *Proc Soc Erp Med*, vol. 130, 1969, pp. 1327-1332.

Huskisson et al., "Ibuprofen, A Review", *Practitioner*, vol. 207, 1971, pp. 639-643.

Brooks et al., "Tolerance and Pharmacology of Ibuprofen", *Current Therapeutic Research*, vol. 15, No. 4, Apr. 1973, pp. 180-190.

"Summary Basis of Approval of NUPRIN", 1984, NDA 19-012, Section IV, p. 2 and Section V, pp. 3-27.

Motrin, Physician's Desk Reference, 41st Edition, 1987, pp. 2058-2060.

Sheth et al., "Measurement of Antipyretic Activity of Ibuprofen and Paracetamol in Children", *J Clin Pharmacol*, vol. 20, 1980, pp. 672-675.

Gaitonde et al., "Antipyretic Activity of Ibuprofen (BRUFEN)", *J Assoc Physicians India*, vol. 21, 1973, pp. 579-584.

Simila et al., "Oral Antipyretic Therapy, Evaluation of Ibuprofen", *Scand J Rheumatology*, vol. 5, 1976, pp. 81-83.

Phadke et al., "Ibuprofen in Children with Infective Disorders-Antipyretic Efficacy", *Br J Clin Pract*, Nov.-Dec. 1985, pp. 437-440.

Amdekar et al., "Antipyretic Activity of Ibuprofen and Paracetamol in Children with Pyrexia", *Brit J Clin Pract*, Apr. 1985, pp. 140-143.

(List continued on next page.)

*Primary Examiner*—Nancy A. B. Swisher
*Attorney, Agent, or Firm*—Indyk, Pojunas & Brady

[57] ABSTRACT

A clear, stable, and palatable liquid ibuprofen composition has ibuprofen, or a pharmaceutically acceptable salt or ester of ibuprofen, in an aqueous medium containing a methylcellulose composition. A process of making such an ibuprofen composition is significantly simpler and less expensive to carry out than prior processes of making liquid ibuprofen compositions. The liquid ibuprofen composition may also contain pharmaceutically acceptable alcohol, dispersing and suspending agents, viscosity increasing agents, flavorings, and preservatives.

46 Claims, No Drawings

OTHER PUBLICATIONS

Kandoth et al., "Comparative Evaluation of Antipyretic Activity of Ibuprofen and Aspirin in Children with Pyrexia of Varied Aetiology", *J Int Med Res*, vol. 12, 1984, pp. 292-297.

Kotob, "A Comparative Study of Two Dosage Levels of Ibuprofen Syrup in Children with Pyrexia", *J Int Med Res*, vol. 13, 1985, pp. 122-126.

Adams et al., "Some Biological Properties of 2-(-4-Isobutylphenyl)-Propionic Acid", *J Pharm Sci*, vol. 56, 1967, p. 1686.

Davis, "Drug Evaluation Data, Ibuprofen", *Drug Intelligence and Clinical Pharmacy*, vol. 9, 1979, pp. 501-503.

Adams et al., "Ibuprofen and Flurbiprofen", *Clinics in Rheumatic Diseases*, vol. 5, No. 2, Aug. 1979, pp. 359-379.

Greenblatt et al., "Absorption and Disposition of Ibuprofen in the Elderly", *Arthritis and Rheumatism*, vol. 27, No. 9, Sep. 1984, pp. 1066-1069.

Whitehall Company Product Monograph, ADVIL, 1984, p. 43.

Blechman et al., "Ibuprofen or Aspirin in Rheumatoid Arthritis Therapy", *Journal of the American Medical Association*, vol. 233, pp. 336-339.

Dornan et al., "Comparison of Ibuprofen and Acetylsalicylic Acid in the Treatment of Rheumatoid Arthritis", *CMA Journal*, vol. 110, Jun. 22, 1974, pp. 1370-1372.

Royer et al., "A Six-Month Double-Blind Trial of Ibuprofen and Indomethacin in Osteoarthritis", *Current Therapeutic Research*, vol. 17, No. 2, Mar. 1975, pp. 234-248.

Muckle, "Comparative Study of Ibuprofen and Aspirin in Soft-Tissue Injuries", *Rheumatol. and Rehab.*, vol. 13, 1974, pp. 141-147.

Abstract of Vecchio et al., "Efficacy of Ibuprofen in Muscle Contraction Headache", *Clinical Pharmacology & Therapeutics*, vol. 33, No. 2, 1983, p. 199.

Shapiro et al., "The Effect of Ibuprofen in the Treatment of Dysmenorrhea", *Curr. Ther. Res.*, vol. 30, pp. 327-333.

Cooper et al., "Comparative Analgesic Potency of Aspirin and Ibuprofen", *J. Oral Surgery*, vol. 35, Nov. 1977, pp. 898-903.

Bloomfield et al., "Comparative Efficacy of Ibuprofen and Aspirin of Episiotomy Pain", *Clin Pharmacol Ther*, vol. 15, 1974, pp. 565-570.

Perry et al., "Ibuprofen Overdose: The First Two Years of Over-The-Counter Sales", *Human Toxocol.*, vol. 6, 1987, pp. 173-178.

Hall et al., "Ibuprofen Overdose: 126 Cases", *Annals of Emergency Medicine*, vol. 15, Nov. 1986, pp. 1308-1313.

Bibliography (1966 to Apr. 1988) obtained from a Search of the Medline Computer Data Base Calling for All Documents with the Word "Ibuprofen" in the titles. Computer printouts resulting from searches of the following computer data bases of documents containing in words "Ibuprofen" and any of Child, Pediatric, or Infant: Dialog, Medline, International Pharmaceutical Abstracts, Pharmaceutical News Index, and Clinical Abstracts.

LIQUID IBUPROFEN COMPOSITIONS AND METHODS OF MAKING THEM

FIELD OF INVENTION

This invention relates to liquid ibuprofen compositions and processes of making them. More specifically, this invention relates to liquid ibuprofen compositions which are clear, stable, palatable, and simple and economical to make. These compositions are useful in treating pain, inflammation, and fever. They may be used in conjunction with other medications, such as cough medications, cold medications, antihistamines, decongestants, or narcotics, or with any combinations of two or more of these medications. Although anyone may partake of their advantages, these compositions are particularly useful in treating patients unable to swallow solid dosages of ibuprofen, such as the very young, the very old, and the infirm.

BACKGROUND OF THE INVENTION

Ibuprofen (p-isobutylhydratropic acid) is a nonsteroidal composition that has long been recognized as being useful in the treatment of pain, inflammation, and fever. More particularly, ibuprofen has been found in clinical studies to be very effective in the treatment of the signs and symptoms of rheumatoid arthritis and osteoarthritis, the relief of mild to moderate pain, and the treatment of primary dysmenorrhea, among other things. Ibuprofen is at least as effective as other available high potency compounds, such as indomethacin and phenylbutazone, but without their attendant side effects, such as increased toxicity. Also, ibuprofen is obtainable over the counter in certain dosages, whereas other high potency compounds are not.

Dosages of ibuprofen have been available in the marketplace only in solid form such as in a tablet or a capsule form. There are significant segments of the population, however, which are unable to conveniently take medication in solid form. These include the pediatric population, the geriatric population, the infirm, and those who for whatever reason cannot or prefer not to swallow solid dosages of medication. For these people, the benefits of ibuprofen have been effectively unavailable because of the unavailability of liquid forms of the composition. Until this time, attempts to meet the needs of these people involved use of other analgesic compositions in liquid form such as liquid acetaminophen and liquid aspirin compositions. These efforts have been largely ineffective because the analgesia produced by these compositions is less than that obtainable with ibuprofen, acetaminophen compositions lack anti-inflammatory activity, and aspirin has come into disfavor because it causes gastrointestinal discomfort in some patients and it has been reported to be linked to Rye's syndrome in children.

In response to this long standing need, there have been many attempts to provide a liquid ibuprofen composition. For the most part, these attempts have been frustrated by the facts that ibuprofen is insoluble in water, has a very bitter taste, and is unstable in aqueous media.

Nicholson U.S. Pat. No. 3,385,886 refers to (1) a mixture of sodium 4-isobutylphenylacetate, orange peel infusion, and chloroform water, (2) a suspension of 4-isobutylphenylacetic acid and tragacanth powder in chloroform water, and (3) an elixir containing, among other things, sodium 4-cyclohexylphenylacetate, ethanol, and glycerol. These compositions all have limited shelf life, poor flavor, and substantial turbidity. Also, those compositions containing chloroform are unsuitable for administration to children and the elderly.

Mueller U.S. Pat. No. 4,447,451 refers to syrups, elixirs, and suspensions of ibuprofen. It says that water soluble forms of ibuprofen can be dissolved in an aqueous vehicle together with sugar, flavoring agents, and preservatives to form a syrup. It also says that an elixir may be prepared by using a hydroalcoholic vehicle, a sweetener, and a flavoring agent. It also says that a suspension may be prepared for insoluble forms of ibuprofen in a "suitable vehicle" with the aid of a suspending agent such as acacia, tragacanth, methylcellulose, and the like. No information is given regarding the nature of the "suitable vehicle". The patent completely fails to appreciate the problems of turbidity and stability that have to be addressed before a suitable liquid ibuprofen composition may be developed. In contrast to the invention of this application, the Mueller patent completely fails to appreciate how methylcellulose compositions are particularly useful in overcoming problems of prior liquid ibuprofen compositions and fails to teach any way of using methylcellulose compositions to overcome those problems. The Mueller patent's complete failure to suggest the invention of this application and its advantages is demonstrated by the specific recipe for an ibuprofen suspension given in the patent. That suspension is to be taken orally and gives a 100 mg. dose of ibuprofen per 5 ml. dose of suspension. It includes an aluminum salt of ibuprofen, citric acid, benzoic acid, sucrose, tragacanth, lemon oil, and deionized water. This composition is cloudy and not chemically stable for any length of time.

Arnold U.S. Pat. No. 4,571,400 refers to pharmaceutical compositions containing dihydrocodeine and ibuprofen. It says that those compositions may have every imaginable ingredient and physical characteristic. Specifically, those compositions, among other things, allegedly may be in liquid form, supposedly as solutions, suspensions, emulsions, syrups, elixirs, or pressurized compositions. The active ingredient allegedly can be dissolved or suspended in a pharmaceutically acceptable liquid carrier such as water, an organic solvent, a mixture of both, or pharmaceutically acceptable oils or fats. There is no indication of how any of this is to be accomplished. The liquid carrier may contain a host of different pharmaceutical additives such as solubilisers, emulsifiers, buffers, preservatives, sweeteners, flavoring agents, suspending agents, thickening agents, colors, viscosity regulators, stabilisers, or osmoregulators. No idea is given about which of these ingredients are to be used, in what amounts they are to be used, or what characteristics would result if they were tried. Purported examples of liquid carriers for oral administration include water said to contain the additives listed above, for example, cellulose derivatives, preferably some unspecified sodium carboxymethylcellulose solution. Alcohols and their derivatives, and oils, are also said to be suitable liquid carriers. There is absolutely no recipe for preparing any liquid composition and Applicant is unaware of the existence of any such recipe apart from the invention of this application which may be used in conjunction with the wish list of the Arnold patent to prepare a liquid ibuprofen composition anything like that of this application. In the Examples, the Arnold patent only purports to describe how to prepare tablets and capsules, and not liquid compositions.

Arnold U.S. Pat. No. 4,587,252 refers to a pharmaceutical composition containing hydrocodone and ibuprofen. The patent purports to describe the entire spectrum of liquid compositions said to be possible for the compositions of the Arnold '400 patent and, like the Arnold '400 patent, gives no idea about how to achieve any of those liquid compositions or what one would get if one were to try to do so.

Moore et al. report a clinical trial using an aluminum ibuprofen suspension to relieve the pain of dental extractions in children (International Journal of Clinical Pharmacology, Therapy and Toxicology, Vol. 23, No. 11-1985, pp. 573-577). No formulation for the suspension is given in the paper, although the paper does indicate that dosages of 200 mg. of ibuprofen were administered. A footnote indicates that the suspension was prepared by the assignee of the Mueller patent.

Haas U.S. Pat. No. 4,684,666 is not prior art, but it is referred to here to give some idea of the background of this invention. It refers to a stabilized liquid ibuprofen composition. Although the patent refers to a completely suitable ibuprofen composition in terms of taste, stability, and lack of turbidity, and in fact describes the first commercially acceptable liquid ibuprofen composition, Applicant has unexpectedly found that the clarity and stability of that ibuprofen composition can be improved upon with the invention of this application. In addition to improved clarity and stability, the invention of this application permits production of the ibuprofen composition with dramatically reduced labor costs in a process of markedly increased simplicity. This permits the marketing of a more palatable liquid ibuprofen composition of reduced cost particularly attractive for parents with small children, elderly people on fixed incomes, and sick persons burdened with high health care costs.

SUMMARY OF THE INVENTION

It is an object of the invention to provide a novel liquid ibuprofen composition and a novel method of making that composition.

It is a further object of the invention to provide a novel liquid ibuprofen composition which is simpler and more economical to make than any such composition proposed in the past.

It is an additional object of the invention to provide a liquid ibuprofen composition which is clear and chemically and physically stable.

It is yet an additional object of the invention to provide an ibuprofen composition in which the control of pH is not a critically important factor.

It is another object of the invention to provide a liquid ibuprofen composition which does not use expensive hydrophilic emulsifying agents or colloidal clays to disperse and suspend the ibuprofen in a liquid medium.

It is an additional object of the invention to provide a liquid ibuprofen composition which avoids the use of antioxidants.

Other objects and advantages are either specifically described elsewhere in this application or are apparent from the description in the application.

In accordance with these objects and advantages, a composition of matter is disclosed and claimed. That composition comprises an ibuprofen composition dispersed and suspended, or dissolved, in an aqueous medium comprising a methylcellulose composition. Also in accordance with these objects and advantages, a method of making such a composition is disclosed and claimed.

DETAILED DESCRIPTION OF THE INVENTION

Liquid ibuprofen compositions in accordance with the invention may contain a therapeutically effective amount of ibuprofen, or a pharmaceutically acceptable salt or ester of ibuprofen, dispersed and suspended in an aqueous medium. Specific examples of such compositions may contain approximately 25 to 400 mg. of ibuprofen per 5 ml. sample of the composition.

The aqueous medium contains a predetermined amount of a methylcellulose composition which acts to suspend the ibuprofen in the aqueous medium. A specific example of a methylcellulose composition suitable for use with this invention is solid sodium carboxymethylcellulose powder. In addition to suspending the ibuprofen in the aqueous medium, the methylcellulose composition assists in the dispersal of the ibuprofen in the medium during preparation of liquid compositions in accordance with this invention. In effect, the methylcellulose composition renders the ibuprofen soluble in the aqueous medium. After formulation of the liquid composition, the methylcellulose composition forms a chemical barrier around the ibuprofen particles suspended in the medium, which prevents the ibuprofen from chemically reacting with the other ingredients in the medium and thus stabilizes the liquid composition of the invention. The methylcellulose also increases the viscosity of the resulting composition.

The amount of methylcellulose to be used in any given situation should be determined by empirical testing and depends on the desired properties of the resulting composition. Specifically, enough should be used to produce the desired amount of dispersion, suspension, solubility, and stability of the ibuprofen in the aqueous medium. Specific examples of the quantity of methylcellulose which Applicant has found to produce good results are described in Examples 1-6 below.

In addition to the methylcellulose composition, the aqueous medium may also contain a pharmaceutically acceptable alcohol to increase the solubility of the ibuprofen in the medium. Such alcohol may also be used to retard microbial growth. One suitable alcohol is ethyl alcohol. The amount of alcohol used should be an amount which produces a desired amount of solubility of ibuprofen and inhibition of microbial growth in the liquid composition. Specific amounts of alcohol which Applicant has found suitable are given in Examples 1-6 below.

In some instances, use of an alcohol in a liquid ibuprofen composition may be undesirable, for example, in a situation where the patient for some reason cannot consume alcohol. It has been found that the alcohol may be eliminated and still a clear, stable, and palatable liquid ibuprofen composition will be obtained.

A bicarbonate composition may also be added to the aqueous medium to assist in the dispersion of the ibuprofen during the formulation of the composition. A suitable bicarbonate composition is potassium bicarbonate. Normally, bicarbonate compositions are used to adjust pH of a solution. In this instance, however, the bicarbonate is not used for the control of pH, but to disperse the ibuprofen in the medium and help it go into solution. The amount to be used is determined in empirical studies of the amounts needed to produce a desired amount of dispersion.

Since ibuprofen has a very bitter taste, it is desirable to mask its flavor. This may be accomplished by the addition of one or more flavoring agents which will accomplish this. One of these flavoring agents may be a sweetener, such as sucrose, which may be added to the medium not only to mask the unpleasant flavor of the ibuprofen, but also to increase the viscosity of the composition so that a syrup results. To enhance the stability and shelf life of ibuprofen compositions of this invention, and to produce a haze free composition, it is suggested that, if sucrose is used, it be of high purity. An example of such a sucrose is Bottler's Grade Extra Fine, No Floc, sold by Holly Sugar.

Some patients may not be able to tolerate high levels of sucrose. In that case, an artificial sweetener may be used in the invention of this application instead of sucrose. Such artificial sweeteners include sodium saccharine and aspartame. If these sweeteners are used, however, it may be desirable to add a composition such as glycerol, sorbitol, propylene glycol, or combinations of two or more of those ingredients in an amount which will build up the viscosity of the resulting composition.

In addition to sweetening the composition of the invention to mask the flavor of the ibuprofen, other ingredients may be added to enhance its flavor and mouthfeel. One possibility is menthol. Another is glycerin, which is also useful as a dispersing and suspending agent for the ibuprofen in the aqueous medium. It also increases the viscosity of the composition. Fruit flavorings may also be added to the composition, such as banana, cherry, or citrus fruit flavorings. Licorice, bubble gum, selected spices, such as cinnamon, and a mint, such as peppermint, may also be used to flavor the liquid ibuprofen composition. The flavorings may be natural or artificial flavorings.

Although the pharmaceutically acceptable alcohol mentioned above will inhibit microbial growth, it may also be advisable to add an additional preservative to compositions in accordance with the invention of this application. It may be even more desirable to do so when an alcohol is not used. Such additional preservatives include paraben compositions such as methyl, butyl, and propyl parabens. A mixture of methyl paraben and propyl paraben in a one part propyl paraben to two parts methyl paraben by weight mixture has been found desirable.

Compositions in accordance with the invention of this application are liquid ibuprofen compositions exhibiting a great deal of clarity without haze formation. They are chemically and physically stable for extended periods of time. In other words, the ibuprofen tends not to chemically react with anything either inside or outside the liquid medium. It remains dispersed and suspended in the medium and does not settle to the bottom of the container in which the composition is stored. For all intents and purposes, liquid ibuprofen compositions in accordance with this invention are stable aqueous solutions of ibuprofen, something which Applicant is unaware of actually having been produced before. No particulate matter is evident under visual inspection and the ibuprofen is uniformly dispersed and suspended in the aqueous medium. This condition is maintained for extended periods of time.

No expensive hydrophilic emulsifying agents and colloidal clays are required to produce these compositions, nor are any special antioxidants required, such as metabisulfites, which some have claimed may cause allergic reactions in children. Also, it is not critical that pH be controlled. The composition is simpler and less expensive to make than prior liquid ibuprofen compositions, perhaps less expensive by as much as 50% of the cost of producing prior liquid ibuprofen compositions.

Compositions in accordance with the invention of this application may be prepared by the following process. First, a predetermined amount of water is measured into a vessel, which is then heated to a temperature which will aid in the dispersal of the ingredients in the liquid medium, for example 55° C. to 65° C. Then, a predetermined amount of methylcellulose composition is measured and slowly added to the heated water while it is being stirred. Once the methylcellulose composition has been completely dissolved, a desired amount of sweetener may be measured out and slowly added to the heated aqueous methylcellulose solution until it is all dissolved in the solution. The solution then is removed from the source of heat and allowed to cool. It may be necessary to allow the solution to cool overnight. The rest of the process steps may be carried out at the elevated temperatures described above, but it is desirable to allow the solution to cool in this manner because the ibuprofen to be added later is more easily dissolved in the solution at lower temperatures. Specifically, the finely milled ibuprofen has less of a tendency to clump and less froth is produced when the ibuprofen is added to the solution. There is also less risk of degrading the ibuprofen at lower temperatures.

After the solution is allowed to cool, a preselected amount of a bicarbonate composition may be weighed out and added slowly to the cooled solution as it is being mixed at high speed. Next, a desired amount of finely ground ibuprofen is weighed out and slowly added to the solution as it is being mixed. At this time, foam appears in the solution which now appears to have a milky color. After the ibuprofen is added to the solution, it is mixed at high speed for a predetermined time, for example, 10 minutes. After the expiration of this mixing time, a predetermined amount of glycerin may be measured out and added to the solution. Another predetermined period of high speed mixing may follow, for example 5 minutes, followed by the addition of a predetermined amount of the pharmaceutically acceptable alcohol and continued mixing for an additional period of time, such as 5 minutes. A desired amount of preservative, such as a paraben composition may be added at this time.

Next, menthol may be dissolved in another predetermined amount of the pharmaceutically acceptable alcohol or in a predetermined amount of water heated to a temperature which will promote the dissolving of the menthol in the water, for example, about 55° C. to 65° C. The resulting menthol solution may be added to the liquid ibuprofen composition as it is being mixed. The parabens may be added to the menthol solution before it is added to the liquid ibuprofen composition, instead of directly to the ibuprofen composition as described above. Additional flavoring may be added at this time, such as banana flavoring.

After all of these ingredients have been combined, the resulting composition should be mixed at high speed until all of the ingredients have been thoroughly mixed together, for example, the composition may be mixed for an additional 10 minutes. After such mixing, the composition should be allowed to stand for a predetermined time until the foam has dissipated and all the gaseous components in the liquid are evaporated off, at which time a clear solution appears, which perhaps will have a tinge of color depending on the nature of the flavoring employed. No particles of ibuprofen are evident upon visual examination. In this condition, a filtering aid may be added to the composition and the composition may be passed through a filter to remove any other particulate impurities that may be present. Filtering apparatus to accomplish this may be obtained from companies such as Sparkler or Millipore. The composition may be filtered through a filter paper which may have a layer of 17 micron cotton rag paper underlined with a 40 micron lint free rayon cellulose binder. The composition may then be inspected for quality and packaged in a covered glass container.

EXAMPLE 1

A 250 liter batch of a liquid ibuprofen composition in accordance with the invention of this application may be prepared as follows. The resulting composition will contain about 400 mg. of ibuprofen per 5 ml. of the liquid composition (about a teaspoonful sample of the composition). A list of the ingredients needed for the preparation of this batch is as follows:

| Ingredient | Quantity |
| --- | --- |
| Ibuprofen milled (60 mesh) | 20,000 gm. |
| Sodium carboxymethylcellulose 7 MF | 750 gm. |
| Sucrose NF XVI | 125,000 gm. |
| Potassium bicarbonate USP XXI powder | 11,500 gm. |
| Glycerin USP XXI (96%) | 12,500 ml. |
| Ethyl alcohol 190 proof USP XXI | 40,400 ml. |
| Methyl paraben USP XVI | 200 gm. |
| Propyl paraben USP XVI | 100 gm. |
| Menthol USP XXI | 100 gm. |
| Banana flavor F1201 (Givaudan) | 1000 ml. |
| Purified water USP XXI | 100,000 ml. |
| Dicelite Speedex filter aid | 300 gm. |

Before preparing the composition, the preparation area should be checked for cleanliness, including all equipment coming in contact with the ingredients. In addition to the raw materials listed above, the following equipment should be available:
1. Fitzmill;
2. 80 gallon jacketed tank;
3. 100 gallon tank;
4. Transfer pump and hoses; and
5. Sparkler filter To avoid microbial contamination, contact of the ingredients and the equipment with the hands should be avoided.

The purified water is placed in the 80 gallon tank which has been fitted with a double impeller stirrer. The stirrer has an impeller toward the bottom of the tank and an impeller toward the top of the tank so that adequate mixing is obtained from top to bottom in the tank. The water in the tank is then heated to a temperature of about 55° C. to 65° C.

The 750 grams of sodium carboxymethylcellulose powder then are slowly added to the heated water while it is being stirred at high speed. Once this powder has dissolved completely, then the 125,000 gm. of sucrose are slowly added to the solution while it is stirred at high speed. When the sucrose has been dissolved, the solution is permitted to cool until it has a temperature of about 20° C. to 30°C.

Using a Fitzmill with a screen and its hammers forward, 11,500 grams of potassium bicarbonate powder are milled into a tared container. Then the potassium bicarbonate powder is added to the processing tank while the contents of the tank continues to be stirred. After the potassium bicarbonate has been dissolved, then the milled ibuprofen is slowly added to the tank while the contents of the tank is being stirred. Glycerin then may be added to the tank which undergoes continued stirring. The tank then is allowed to stand until the froth that has appeared has subsided. If the froth does not subside, the mixture should be stirred again and allowed to stand until it becomes clear.

Next, the ethyl alcohol is placed in a suitable stainless steel vessel. The methyl paraben, propyl paraben, and menthol are then dissolved in the alcohol. Stirring is used to aid in dissolving these ingredients. Flavoring such as banana flavoring is added to the alcohol at this time. The alcoholic solution is then added to the main processing tank while its contents are being stirred at high speed. More deionized water is then added to the tank so that the contents of the tank is 250 liters of liquid ibuprofen composition. A calibrated dip stick may be used to measure the amount of liquid in the tank. When 250 liters of liquid are in the tank, it is mixed thoroughly for about ten minutes.

A Sparkler filter Model 18-S-7 is then set up according to manufacturer's instructions using filter paper having one layer of 17 micron cotton rag underlined by a 40 micron lint free rayon cellulose binder. Dicelite Speedex filter aid is added to the batch which is then mixed for ten minutes. The batch then is filtered into a clean 100 gallon stainless steel tank, which then may be sealed to prevent loss of volatiles.

A clear, stable, and palatable liquid ibuprofen composition having about 400 mg. of ibuprofen per 5 ml. sample results at this time.

EXAMPLE 2

A 250 liter batch of a liquid ibuprofen composition containing about 25 mg. of ibuprofen per 5 ml. of the composition may be prepared in accordance with the steps of Example 1 with the exception that 1,250 grams of ibuprofen is used instead of the 20,000 grams of ibuprofen specified in Example 1. Using 2,500 grams of ibuprofen in this Example instead of 1,250 grams will result in a liquid composition having about 50 mg. of ibuprofen per 5 ml.

EXAMPLE 3

A 250 liter batch of a liquid ibuprofen composition containing about 100 grams of ibuprofen per 5 ml. may be prepared in accordance with the steps of Example 1 with the exception that 5,000 grams of ibuprofen is used instead of the 20,000 grams of ibuprofen specified in Example 1. Using 10,000 grams of ibuprofen in this Example instead of 5,000 grams will result in a liquid composition having about 200 mg. of ibuprofen per 5 ml.

EXAMPLE 4

A 250 liter batch of a liquid ibuprofen composition containing about 400 mg. of ibuprofen per 5 ml. sample of the composition may be prepared in accordance with the steps of Example 1 with the exception that no ethyl alcohol is used. The methyl paraben and propyl paraben are added directly to the batch and the menthol is added to water heated to 55° C. to 65° C. and dissolved in the heated water before being added to the batch. 250 liter batches of liquid ibuprofen composition containing about 25 mg., 50 mg., 100 mg., and 200 mg. of ibuprofen per 5 ml. sample of the composition may be prepared in accordance with Examples 2 and 3, as modified by the exception to the steps of Example 1 specified in this Example.

EXAMPLE 5

A 250 liter batch of a liquid ibuprofen composition containing about 400 mg. of ibuprofen per 5 ml. sample of the composition may be prepared in accordance with the steps of Example 1 with the exception that no ethyl alcohol or menthol is used. The methyl paraben and propyl paraben are added directly to the batch. 250 liter batches of liquid ibuprofen composition containing about 25 mg., 50 mg., 100 mg., and 200 mg. of ibuprofen per 5 ml. sample of the composition may be prepared in accordance with Examples 2 and 3, as modified by the exception to the steps of Example 1 specified in this Example.

EXAMPLE 6

A 250 liter batch of a liquid ibuprofen composition containing about 400 mg. of ibuprofen per 5 ml. sample of the composition may be prepared in accordance with the steps of Example 1 with the exception that no potassium bicarbonate is used and no flavoring agent is used apart from the sucrose. It has been surprisingly found that the sucrose is able to almost completely mask the unpleasant flavor of the ibuprofen in this example of the invention. 250 liter batches of liquid ibuprofen composition containing about 25 mg., 50 mg., 100 mg., and 200 mg. of ibuprofen per 5 ml. sample of the composition may be prepared in accordance with Examples 2 and 3, as modified by the exception to the steps of Example 1 specified in this Example.

I claim:

1. An aqueous solution of ibuprofen, comprising: a predetermined therapeutically effective amount of an ibuprofen composition dissolved in an aqueous medium comprising a predetermined amount of a bicarbonate composition, the therapeutically effective amount of the ibuprofen composition being such that there is approximately 25 mg. to 400 mg. of the ibuprofen composition per 5 ml. of the aqueous solution of ibuprofen.

2. The solution of claim 1, in which the bicarbonate composition comprises potassium bicarbonate.

3. The composition of claim 1, on which the predetermined amount of bicarbonate composition is such that the ibuprofen composition goes into solution and a clear aqueous solution of ibuprofen composition results.

4. A clear liquid composition of matter, comprising: a therapeutically effective amount of an ibuprofen composition dissolved in an aqueous medium containing a methylcellulose composition, a bicarbonate composition, a sweetener, glycerin, a flavoring agent, and a preservative composition, all of these ingredients being dissolved in the aqueous medium in a manner such that the no particulate matter is evident upon visual examination, the therapeutically effective amount of the ibuprofen composition being such that there is approximately 25 mg. to 400 mg. of the ibuprofen composition per 5 ml. of the clear liquid composition of matter.

5. The clear liquid composition of claim 4, in which the ibuprofen composition is selected from the group consisting of ibuprofen and the pharmaceutically acceptable salts and esters of ibuprofen.

6. The clear liquid composition of claim 4, in which the methylcellulose composition comprises sodium carboxymethylcellulose.

7. The clear liquid composition of claim 6, in which the sweetener is sucrose.

8. The clear liquid composition of claim 7, in which sweetener further comprises saccharine.

9. The clear liquid composition of claim 8, in which the sweetener further comprises saccharine.

10. The clear liquid composition of claim 8, in which the sweetener further comprises an artificial sweetener.

11. The clear liquid composition of claim 4, in which the bicarbonate composition is an alkali metal bicarbonate composition.

12. The clear liquid composition of claim 4, in which the bicarbonate composition is potassium bicarbonate.

13. The clear liquid composition of claim 4, in which the sweetener is sucrose.

14. A liquid ibuprofen composition, comprising: an aqueous medium; and a therapeutically effective amount of an ibuprofen composition dissolved in the aqueous medium so that no particulate matter is evident in the liquid composition upon visual examination, the therapeutically effective amount of the ibuprofen composition being such that there is approximately 25 mg. to 400 mg. of the ibuprofen composition per 5 ml. of the liquid ibuprofen composition.

15. The liquid ibuprofen composition of claim 14, in which the aqueous medium comprises a bicarbonate composition.

16. The liquid ibuprofen composition of claim 15, in which the bicarbonate composition is potassium bicarbonate.

17. The liquid ibuprofen composition of claim 15, in which the aqueous medium further comprises a methylcellulose composition and a sweetening agent.

18. The liquid ibuprofen composition of claim 17, in which the methylcellulose composition is sodium carboxymethylcellulose and the sweetening agent is sucrose.

19. The liquid ibuprofen composition of claim 17, in which the aqueous medium further comprises glycerine.

20. The liquid ibuprofen composition of claim 19, in which the aqueous medium further comprises a flavoring agent.

21. A liquid ibuprofen composition, prepared by a process comprising the steps of: dissolving a dispersing agent in an aqueous medium; and dissolving a therapeutically effective amount of an ibuprofen composition in the aqueous medium so that no particulate matter is evident in the liquid composition upon visual examination, the therapeutically effective amount of the ibuprofen composition being such that there is approximately 25 mg. to 400 mg. of ibuprofen composition per 5 ml. of the liquid ibuprofen composition.

22. The composition of claim 21, in which the dispersing agent comprises a bicarbonate composition.

23. The liquid ibuprofen composition of claim 22, in which the bicarbonate composition is potassium bicarbonate.

24. The liquid ibuprofen composition of claim 22, in which the aqueous medium further comprises a methylcellulose composition and a sweetening agent.

25. The liquid ibuprofen composition of claim 24, in which the methylcellulose composition is sodium carboxymethylcellulose and the sweetening agent is sucrose.

26. The liquid ibuprofen composition of claim 24, in which the aqueous medium further comprises glycerine.

27. The liquid ibuprofen composition of claim 26, in which the aqueous medium further comprises a flavoring agent.

28. A clear, stable, and palatable liquid composition of matter, comprising:
   a therapeutically effective amount of an ibuprofen composition dissolved in an aqueous medium comprising a bicarbonate composition, the ibuprofen composition being dispersed in the liquid composition so that no particulate matter is evident upon visual examination, the therapeutically effective amount of the ibuprofen composition being such that there is approximately 25 mg. to 400 mg. of ibuprofen composition per 5 ml. of the liquid ibuprofen composition of matter.

29. The composition of claim 28, further comprising a methylcellulose composition and a sweetening agent.

30. The composition of claim 28, in which the bicarbonate composition is potassium bicarbonate.

31. The composition of claim 29, in which the bicarbonate composition is potassium bicarbonate.

32. A clear, stable, and palatable aqueous ibuprofen solution, comprising:
   a therapeutically effective amount of an ibuprofen composition dissolved in an aqueous medium comprising a bicarbonate composition, the ibuprofen composition being dissolved in the liquid composition so that no particulate matter is evident upon visual examination, the therapeutically effective amount of the ibuprofen composition being such that there is approximately 25 mg. to 400 mg. of ibuprofen composition per 5 ml. of the ibuprofen solution.

33. The ibuprofen solution of claim 32, in which the bicarbonate composition is potassium bicarbonate.

34. A clear aqueous ibuprofen solution, prepared in accordance with a process comprising the steps of:
   heating a predetermined amount of water to a predetermined temperature;
   dissolving a predetermined amount of a solid methylcellulose composition in the heated water;
   dissolving sucrose in the heated methylcellulose solution;
   dissolving a bicarbonate composition in the solution of methylcellulose and sucrose; and
   dissolving a predetermined therapeutically effective amount of an ibuprofen composition in the solution of methylcellulose and sucrose, the therapeutically effective amount of the ibuprofen composition being such that there is approximately 25 mg. to 400 mg. of ibuprofen composition per 5 ml. of the ibuprofen solution.

35. The solution of claim 34, in which the bicarbonate composition is potassium bicarbonate.

36. The solution of claim 34, in which the methylcellulose composition is sodium carboxymethylcellulose.

37. The solution of claim 36, in which the bicarbonate composition is potassium bicarbonate.

38. The solution of claim 37, in which the amount of potassium bicarbonate composition used is an amount sufficient to dissolve the ibuprofen composition in the water.

39. The solution of claim 36, in which the amount of bicarbonate composition used in an amount sufficient to dissolve the ibuprofen composition in the water.

40. A liquid ibuprofen composition, prepared in accordance with a process comprising the steps of:
   dissolving a predetermined amount of a bicarbonate composition in an aqueous medium; and
   dissolving a therapeutically effective amount of an ibuprofen composition in the aqueous medium containing the bicarbonate composition, the therapeutically effective amount of the ibuprofen composition being such that there is approximately 25 mg. to 400 mg. of ibuprofen composition per 5 ml. of the liquid ibuprofen composition.

41. The liquid ibuprofen composition of claim 40, in which the bicarbonate composition is potassium bicarbonate.

42. The liquid ibuprofen composition of claim 40, in which the aqueous medium further comprises a methylcellulose composition and a sweetening agent.

43. The liquid ibuprofen composition of claim 42, in which the methylcellulose composition is sodium carboxymethylcellulose and the sweentening agent is sucrose.

44. The liquid ibuprofen composition of claim 42, in which the aqueous medium further comprises glycerine.

45. The liquid composition of claim 44, in which the aqueous medium further comprises a flavoring agent.

46. A clear, stable, and palatable liquid ibuprofen composition, prepared in accordance with a process comprising the steps of:
   dissolving sodium carboxymethylcellulose and sucrose in an aqueous medium;
   dissolving potassium bicarbonate in the aqueous medium;
   dissolving a predetermined therapeutically effective amount of ibuprofen in the aqueous medium, the therapeutically effective amount of the ibuprofen composition being such that there is approximately 25 mg. to 400 mg. of ibuprofen composition per 5 ml. of the liquid ibuprofen composition;
   dissolving a predetermined amount of glycerin in the aqueous medium; and
   dissolving a flavoring agent and a mixture of methyl paraben and propyl paraben in the aqueous medium.

* * * * *